United States Patent [19]

Sarnow et al.

[11] Patent Number: 5,766,903

[45] Date of Patent: Jun. 16, 1998

[54] CIRCULAR RNA AND USES THEREOF

[75] Inventors: Peter Sarnow, Boulder; Chang-you Chen, Denver, both of Colo.

[73] Assignee: University Technology Corporation, Boulder, Colo.

[21] Appl. No.: 518,189

[22] Filed: Aug. 23, 1995

[51] Int. Cl.$^6$ .............................. C12N 5/00; C12N 15/63; C12N 15/79; C12Q 1/68

[52] U.S. Cl. .................... 435/172.3; 435/6; 435/69.1; 435/91.3; 435/91.52; 435/172.1; 435/320.1; 435/325; 435/375; 435/410; 424/450; 536/23.1; 536/24.1; 514/44

[58] Field of Search ........................... 435/172.3, 172.1, 435/6, 320.1, 7.21, 7.23, 7.24, 7.25, 69.1, 325, 366, 367, 372, 372.1, 375; 514/44; 536/23.1, 24.1; 424/450

[56] References Cited

U.S. PATENT DOCUMENTS 5,580,859 12/1996 Felgner et al. .............................. 514/44

OTHER PUBLICATIONS

R. Harland et al. Development 102: 837–852, 1988.
Jackson et al., 1991, *Nature*, 353:14–16.
Jang et al., 1988, *Journal of Virology*, 62(8):2636–2643.
Kozak, 1992, *Critical Reviews in Biochemistry and Molecular Biology*, 27(4.5):385–402.
Macejak et al., 1991, *Nature*, 353:90–94.
Molla et al., 1992, *Nature*, 356:255–257.
Oh et al., 1992, *Genes & Development*, 6:1643–1653.
Pelletier et al., 1988, *Nature*, 334:320–325.
Rigden et al., In vitro synthesis of an infectious viroid: analysis of the infectivity of monomeric linear CEV. Virology, 1992, Vo. 186, pp. 201–206.
Van Eldik et al., Synthesis and expression of a gene coding for the calcium–modulated protein S100β and designed for cassette–based, site–directed mutagenesis. The Journal of Biological Chemistry. 05 Jun. 1988, vol. 263, No. 16, pp. 7830–7837.

*Primary Examiner*—Charles C. P. Rories
*Attorney, Agent, or Firm*—Sheridan Ross P.C.

[57] ABSTRACT

The present invention relates to a product and process for producing polypeptides, such products including a circular RNA having a ribosome binding site that engages an eukaryotic ribosome and cells transformed with such circular RNA. Circular RNA is produced by linking the 5' and 3' ends of a desired linear RNA sequence, and such constructs can be used to produce desired amounts of polypeptides when such constructs are translated either in vitro or in vivo. The present invention also relates to the use of circular RNA as a pharmaceutical agent to treat cells and animals involved in a disease.

49 Claims, 4 Drawing Sheets

CIRCULAR RNA AND USES THEREOF

GOVERNMENT RIGHTS

This invention was made in part with government support under NIH AI-25105, awarded by the National Institutes of Health. The government has certain rights to this invention.

FIELD OF THE INVENTION

The present invention relates to a product comprising a circular RNA capable of being translated by a eukaryotic ribosome. In addition, the present invention relates to a process for producing a desired polypeptide using a circular RNA of the present invention.

BACKGROUND OF THE INVENTION

General limitations on commercial production of polypeptides include the efficiency of synthesis and, if a complex synthesis process is involved, the proper processing of polypeptides. The advent of recombinant molecular biological techniques has enabled investigators to produce substantial amounts of desired polypeptides in a variety of expression systems. Such expression systems, however, typically include: bacterial cells, from which polypeptides are difficult to recover and eukaryotic polypeptides are not processed (e.g., glycosylated) properly; or eukaryotic cells, in which large amounts of a polypeptide have proven to be difficult to produce.

The use and purification of polypeptides produced by recombinant expression systems creates potentially serious problems since recombinant production of polypeptides has become a mainstay in the development and production of therapeutic and diagnostic reagents. Thus, there is a continuing need for a simpler and commercially efficient method to produce substantial amounts of optimally active recombinant polypeptides for use in experimental, therapeutic and diagnostic applications.

Deoxynucleic acid molecules (DNA) is transcribed into deoxyribonucleic acid molecules (RNA), which in turn is translated into amino acid sequences (polypeptides). Until the discovery of the present invention, linear RNA molecules have been used as experimental tools to study the mechanisms regulating RNA translation. Prior investigators have shown that linear RNA molecules can be translated using an internal ribosome entry site (IRES) element to which eukaryotic ribosomes can bind (see, for example, Jang et al., *J. Virol.* 62:2636–2643, 1988; Pelletier et al. *Nature* 334:320–325, 1988; Jackson, *Nature* 353:14–15, 1991; Macejek et al., *Nature* 353:90–94, 1991; Oh et al., *Genes & Develop.* 6:1643–1653, 1992; Molla et al., *Nature* 356:255–257, 1992; and Kozak, *Crit. Rev. Biochem. Molec. Biol.* 27(4,5):385–402, 1992). These investigators do not teach the production of circular RNAs to which eukaryotic ribosomes can bind, and thus do not disclose the production of desired polypeptides using circular RNA constructs.

Thus, there remains a need to develop a circular RNA capable of binding a eukaryotic ribosome, thereby enabling production of large amounts of desired polypeptides, particularly eukaryotic polypeptides.

SUMMARY OF THE INVENTION

The present invention relates to circular RNA, having a ribosome binding site that engages an eukaryotic ribosome, that is useful for the production of desired amounts of a polypeptide. The invention is particularly advantageous in that it provides a circular construct that can be continuously and repeatedly translated as a ribosome travels around the RNA circle, producing a polypeptide with each pass of the ribosome. Another advantageous aspect of a circular RNA of the present invention is that, unlike linear RNA, circular RNA is not as susceptible to exonuclease activity. Thus, the circular RNA is more stable during storage and use than linear RNA.

One embodiment of the present invention includes a circular RNA having a ribosome binding site that engages an eukaryotic ribosome. Preferably, a circular RNA of the present invention comprises an internal ribosome entry site element derived from picornavirus cDNA, BiP-encoding DNA, Drosophila Antennapedia DNA, and/or bFGF-encoding DNA. A circular RNA of the present invention preferably comprises an RNA sequence encoding a polypeptide.

Another embodiment of the present invention includes a recombinant cell, comprising an RNA having no free ends that engages an eukaryotic ribosome. Preferably, a recombinant cell of the present invention is derived from a host cell including, a Cos cell, kidney cell lines, other fibroblast cell lines, myeloma cell lines, Chinese hamster ovary cells, mouse NIH/3T3 cells, HeLa cells and Jurkat cells.

Yet another embodiment of the present invention includes a delivery vehicle comprising a pharmaceutically acceptable carrier carrying a circular RNA that engages an eukaryotic ribosome. Preferably, a pharmaceutically acceptable carrier of the present invention includes, a physiologically balanced aqueous solution, a cell and/or a lipid construction. Preferred lipid constructions include, liposomes, micelles, and a cellular membranes.

The present invention includes a method to produce a circular RNA, comprising: (1) providing a linear DNA plasmid comprising a nucleic acid sequence that is transcribed into an internal ribosome entry site element; (2) transcribing the DNA plasmid in the presence of guanosine nucleotide to produce linear RNA transcripts; and (3) ligating the transcripts with DNA oligonucleotides complementary to the 5' and 3' ends of the transcript to produce circular RNA. The method further comprises separating the DNA oligonucleotides from the circular RNA. The guanosine nucleotide is preferably a mixture of guanosine mononucleotide and guanosine trinucleotide, preferably at about a 10:1 ratio.

The present invention also includes a method for producing a polypeptide, comprising: (1) translating a circular RNA comprising an internal ribosome entry site element operatively linked to an RNA sequence encoding a polypeptide to produce the polypeptide; and (2) recovering the polypeptide. The translation step can be performed either in vivo or in vitro. A preferred in vivo translation system includes transforming a circular RNA into a cell. A preferred in vitro translation system includes a cell-free system comprising reticulocyte lysate.

Another aspect of the present invention includes a method for using a circular RNA to treat an animal, comprising administering to an animal an effective amount of a circular RNA comprising an internal ribosome entry site element operatively linked to an RNA sequence encoding a polypeptide, wherein the circular RNA is translated to produce the polypeptide in the animal to treat the animal.

Other aspects of the present invention include those embodiments disclosed in the Figures and the detailed description of the present invention.

DETAILED DESCRIPTION OF THE INVENTION

The present invention provides a product and process for producing a polypeptide. In particular, the product includes a circular RNA having a ribosome binding site that engages (i.e., interacts with) an eukaryotic ribosome. The process includes translating the circular RNA to produce a desired polypeptide and recovering the polypeptide.

One embodiment of the present invention is a circular RNA having a ribosome binding site that engages an eukaryotic ribosome. The engagement of the ribosome results in the translation of the RNA. It is to be noted that the term "a" or "an" entity refers to one or more of that entity; for example, a ribosome binding site refers to one or more binding sites or at least one binding site. As such, the terms "a" (or "an"), "one or more" and "at least one" can be used interchangeably herein. It is also to be noted that the terms "comprising", "including", and "having" can be used interchangeably. As used herein, a circular RNA refers to a length of deoxyribonucleic acid having no free ends. The term "circular" is not intended to imply any particular shape or configuration of the RNA. Preferably, a circular RNA of the present invention is single stranded, thereby enabling translation of the RNA.

As a result of its circularization, a circular RNA of the present invention possesses certain characteristics that distinguish it from linear RNA. For example, a circular RNA of the present invention is less susceptible to degradation by exonuclease as compared to linear RNA. As such, a circular RNA of the present invention is more stable than a linear RNA, especially when incubated in the presence of an exonuclease. The increased stability of circular RNA compared with linear RNA makes circular RNA more useful as a cell transforming reagent (discussed in detail below) to produce polypeptides and can be stored more easily and for longer than linear RNA. The stability of an RNA treated with exonuclease can be tested using methods standard in art which determine whether RNA degradation has occurred (e.g., by gel electrophoresis).

Circular RNA also migrates more slowly than linear RNA when the RNAs are resolved by gel electrophoresis using a polyacrylamide gel, preferably about a 4.5% polyacrylamide gel. Resolution of RNA by polyacrylamide gel electrophoresis can be performed using methods known to those of skill in the art.

Moreover, unlike linear RNA, a circular RNA of the present invention is less susceptible to dephosphorylation when the RNA is incubated with phosphatase, preferably calf intestine phosphatase. Treatment of RNA with phosphatase can be performed using methods described in Example 2.

Circular RNA of the present invention is a deoxyribonucleic acid sequence that is non-naturally occurring and can be produced using recombinant DNA technology (methods described in detail below; e.g., derived in vitro using a DNA plasmid) or chemical synthesis. Circular RNA produced using recombinant DNA technology can be derived from any DNA that can be transcribed into RNA. Such DNA can include prokaryotic or eukaryotic DNA and preferably includes, bacterial, fungal, yeast, algal, protozoan, viral, plant or mammalian DNA, with bacterial, viral and mammalian DNA being more preferred. Preferred viral cDNA from which to derive circular RNA includes, but is not limited to, picornavirus, herpes simplex virus (HSV) and human immunodeficiency virus (HIV), with picornavirus DNA being more preferred. Preferred picornavirus DNA from which to derive circular RNA includes, but is not limited to encephalomyocarditis virus, poliovirus and rhinovirus. Preferred mammalian DNA from which to derive circular RNA includes, but is not limited to human, rodent, canine, feline, avian, equine, bovine, swine, and sheep.

It is within the scope of the invention that a DNA molecule used to produce an RNA circle can comprise a DNA sequence of a naturally-occurring original nucleic acid sequence, a modified version thereof, or a DNA sequence encoding a synthetic polypeptide not normally found in nature (e.g., chimeric molecules or fusion proteins). DNA molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof.

The configuration of circular RNA of the present invention can vary substantially. Circular RNA of the present invention can have size limitations dependent upon the ability of a ribosome subunit to engage the RNA in such a manner that results in the translation of the RNA. For example, an RNA circle must be sufficiently large and sterically accessible to allow engagement of a small subunit of a ribosome, which typically has a sedimentation value of about 40S, and sufficiently large enough to engage a large subunit of a ribosome, which typically has a sedimentation value of about 60S, in such a manner that the ribosome can initiate and elongate a polypeptide chain. As used herein, initiation refers to the formation of a complex comprising an RNA, transfer RNA (tRNA), and ribosomal and initiation factors (IF). Elongation follows initiation and involves the addition of additional tRNAs to the engaged ribosome (see discussion in Darnell et al., in *Molecular Cell Biology*, Scientific American Books, 2nd edition, 1990).

Preferably, circular RNA of the present invention is at least about 100 base pairs, more preferably at least about 500 base pairs and even more preferably at least about 1,000 base pairs. A circular RNA must be of a sufficient size to accommodate a binding site for a ribosome. One of skill in the art can appreciate that the maximum size of a circular RNA of the present invention can be as large as is within the technical constraints of producing a circular RNA. For example, if recombinant DNA technology is used to produce a RNA circle, the maximum size of the circle depends upon the ability to transcribe long lengths of linear RNA and anneal any free ends to form a circle (according to the method described below in the Examples section). While not being bound by theory, it is possible that multiple segments of RNA can be produced from DNA and their 5' and 3' free ends annealed to produce a "string" of RNA, which ultimately can be circularized when only one 5' and one 3' free end remains. The maximum size of a circular RNA may be limited by the ability of a ribosome to remain engaged with the RNA as the ribosome progresses down the length of RNA. A preferred size of a circular RNA of the present invention is a length sufficient to encode useful polypeptides, and thus, lengths of about 4,000 base pair, more preferably about 3,000 base pair and even more preferably about 2,000 base pair are believed to be of considerable value.

Circular RNA of the present invention will also necessarily have structural constraints relating to the ability of a ribosome to engage the RNA in such a manner that results in the translation of the RNA. For example, a circular RNA must be configured such that the RNA does not sterically hinder the engagement and progression of a ribosome on the RNA. As used herein, stearic hinderance refers secondary structural constraints of the RNA which interferes with a function (e.g., ribosome engagement or polypeptide elongation). Examples of secondary structures that can result in stearic hinderance include, but are not limited to, RNA helicity formation (i.e., coiling of the RNA) and RNA loop formation (i.e., single stranded RNA annealing to itself to form hairpin loops). Thus, a circular RNA of the present invention, preferably does not sterically hinder the translation of the circular RNA, at least under some predetermined conditions. Purposeful stearic hinderance of circular RNA translation may be performed to temporarily halt undesired translation of such RNA. Thus, it is within the scope of the present invention to adjust conditions so that translation of circular RNA can be controlled and regulated.

It is within the scope of the invention that an RNA circle of the present invention can contain one or more appropriate RNA secondary structures that enable the engagement of a ribosome with the RNA by acting as recognition sites for ribosome binding. Depending upon their placement on the RNA, the secondary structures define an area within which a ribosome will bind to an RNA.

The composition of circular RNA of the present invention can vary substantially. As stated above, the RNA sequence of a circular RNA is related to the DNA sequence from which the RNA is derived. In addition, the ribosome binding site present in a circular RNA can comprise any RNA sequence required to effect the desired engagement of the ribosome. A circular RNA can also contain an RNA sequence encoding a polypeptide. If a circular RNA is transformed into cells, the composition of the circular RNA may include additional regulatory sequences that assist in the translation of the RNA in the cell, as well as in desired post-translational processing of a translated polypeptide.

Circular RNA of the present invention preferably include one or more ribosome binding sites that enables a ribosome to bind to an internal site in an RNA sequence. Traditional mechanisms of ribosome engagement to linear RNA involve ribosome binding to the capped 5' end of an RNA. From the 5' end, the ribosome migrates to a first codon consisting of the nucleotides AUG, whereupon the first peptide bond is formed. Conventional thinking was that this mechanism necessarily required a free 5' end of an RNA. According to the present invention, internal initiation (i.e., cap-independent) of translation of an RNA does not require a free end or a capped end. Rather, a ribosome binds to a non-capped internal site, whereby the ribosome begins polypeptide elongation at an AUG codon. Thus, preferably, a circular RNA of the present invention includes one or more RNA sequences having an AUG codon.

A preferred ribosome binding site of the present invention comprises an internal ribosome entry site (IRES) element. A suitable IRES element to include in a circular RNA of the present invention comprises an RNA sequence capable of engaging an eukaryotic ribosome. Preferably, an IRES element of the present invention is at least about 250 base pairs, more preferably at least about 350 base pairs and even more preferably at least about 500 base pairs. A particularly preferred IRES element of the present invention is derived from the DNA of an organism including, but not limited to, a virus, a mammal, and a Drosophila. Preferred viral DNA from which an IRES element is derived includes, but is not limited to, picornavirus complementary DNA (cDNA), with encephalomyocarditis virus (EMCV) cDNA and poliovirus cDNA being preferred picornavirus cDNA, and EMCV cDNA being more preferred. Preferred mammalian DNA from which an IRES element is derived includes, but is not limited to, DNA encoding immunoglobulin heavy chain binding protein (BiP) and DNA encoding basic fibroblast growth factor (bFGF). Preferred Drosophila DNA from which an IRES element is derived includes, but is not limited to, an Antennapedia gene from *Drosophila melanogaster*.

In a preferred embodiment, a circular RNA of the present invention contains a RNA sequence including, EMCV-IRES/VP3 or EMCV-ORF-IRES/VP3 (as described in detail in the Examples section).

In another embodiment of the present invention, a circular RNA comprises one or more RNA sequences, each of which encode a polypeptide. As used herein, "polypeptides" include peptides (i.e., residue chains of >100 amino acids) and proteins (i.e., residue chains of <100 amino acids). Two or more polypeptides that are directly covalently linked (via peptide bonds) to each other or certain intermediary sequences are referred to herein as "polypeptide chains." Preferably, a polypeptide of the present invention comprises a polypeptide of which one desires to produce substantial amounts. As such, a polypeptide can include any molecule that one wishes to: produce, recover and deliver to a cell. A polypeptide can be a polypeptide that can be secreted from a cell, or localized to the cytoplasm, nucleus or membrane compartment of a cell. Particularly preferred polypeptides include, but are not limited to, at least a portion of a viral envelope protein, metabolic regulatory enzymes (e.g., that regulate lipid or steroid production), an antigen, a toleragen, a cytokine, a toxin, enzymes whose absence is associated with a disease, and polypeptides that are not active in an animal until cleaved (e.g., in the gut of an animal), and a hormone.

According to the present invention, the organization of RNA sequences encoding polypeptides in an RNA circle of the present invention can vary. For example, a circular RNA can contain a single RNA sequence encoding a polypeptide, repeating copies of an RNA sequence encoding the same polypeptide, multiple copies of RNA sequences encoding different polypeptides, or combinations thereof. Translation of circular RNA have such an organization results in the production of polypeptide chains which can be treated with proteases to release individual polypeptides from the polypeptide chain (described in detail below).

In one embodiment, each RNA sequence encoding a polypeptide in an RNA circle is "operatively linked" to a ribosome binding site, preferably an IRES element. The phrase operatively linked refers to insertion of an RNA sequence into an RNA circle in a manner such that the inserted sequence is able to be translated. The resulting polypeptide chain translated from an RNA circle having this organization comprises copies of polypeptides, each copy separated from the next by amino acid sequence encoded by the ribosome binding site.

In another embodiment, each RNA sequence encoding a polypeptide in an RNA circle is directly linked to an intervening sequence typically associated with such RNA sequences. For example, in nature, the gene organization of certain multi-subunit proteins comprises a first DNA sequence encoding a first subunit, directly linked to a first intervening DNA sequence, which in turn is directly linked to a second DNA sequence encoding a second subunit, and so on. Examples of multi-subunit polypeptides using this gene organization include polypeptides having the same repeating subunit (e.g., collagen, elastin and keratin), and polypeptides having different repeating subunits. RNA sequences derived from such DNA-encoding multi-subunit proteins, can be included in a circular RNA of the present invention. The resulting polypeptide chain translated from an RNA circle having this organization comprises copies of polypeptides, separated by amino acid sequence encoding intervening sequences.

If one desires to remove an undesired amino acid sequence between wanted polypeptides in a polypeptide chain, an RNA sequence encoding a proteolytic cleavage site can be inserted between the RNA encoding the polypeptide and the RNA encoding the unwanted amino acid sequence. As such, an RNA circle can contain an RNA sequence encoding a polypeptide, linked to an RNA sequence encoding a proteolytic cleavage site, which in turn is linked to an RNA sequence encoding an undesired amino acid sequence. As used herein, a proteolytic cleavage site refers to an amino acid sequence capable of being cleaved by a protease. Suitable proteolytic cleavage sites include sites that are capable of being cleaved by collagenase, serine proteases, metalloproteases, aspartic acid proteases and/or cysteine proteases, which can be either aminopeptidases, carboxypeptidases or endopeptidases. Preferred proteolytic cleavage sites include, but are not limited to, sites that are capable of being cleaved by kallikriens, plasminogen activators, thrombin, leucine aminopeptidase, aminopeptidases B and M; astacin-like metalloproteases; calpains; carboxypeptidases A, P and Y; cathepsins, chymotrypsins; cruzipains; meprins; papains; pepsins; renins; thermolysins; trypsins; acrosins, bromelains, elastases, factor Xa, ficins, Staphylococcal V8 proteases, clostopain, and imidodipeptidase.

It is also within the scope of the present invention that proteolytic cleavage sites can be inserted into desired regions of a polypeptide to allow for correct folding of a polypeptide upon cleavage by a protease. The advantage of such a system is to temporarily delay the production of a functionally active polypeptide until such time as a skilled artisan chooses to activate such polypeptide.

Preferably, a circular RNA of the present invention does not contain an RNA sequence encoded by a termination codon (e.g., UAA or UGA), thereby allowing continuous translation of the RNA circle. Continuous translation of RNA circles of the present invention allows continuous production of desired polypeptides or polypeptide chains, and thus provides one of the major advantages of the present invention.

In one embodiment, a circular RNA of the present invention is produced by a method comprising: (1) providing a linear DNA plasmid comprising a nucleic acid sequence that is transcribed into an internal ribosome entry site element; (2) transcribing the DNA plasmid in the presence of guanosine nucleotide to produce linear RNA transcripts; and (3) ligating the transcripts with DNA oligonucleotides complementary to the 5' and 3' ends of the transcript to produce circular RNA.

According to the present invention, the DNA plasmid of step (1) comprises a type (e.g., kingdoms, phyla, order, class, genera and species) of DNA as described herein. The plasmid of step (1) contains regulatory sequences such as transcription control sequences, origins of replication, and other regulatory sequences that are compatible with the control of the expression of the plasmid. In particular, the plasmid can include transcription control sequences. Transcription control sequences are sequences which control the initiation, elongation, and termination of transcription. Construction of desired DNA plasmids containing appropriate transcription regulatory sequences can be performed by methods known to those skilled in the art (see, for example, Sambrook et al., *Molecular Cloning: A Laboratory Manual*, Cold Spring Harbor Labs Press, 1989, which is incorporated herein by reference in its entirety) and transcription can be in eukaryotic or prokaryotic systems. Procaryotic systems typically used are bacterial strains including, but not limited to various strains of *E. coli*, various strains of *bacilli* or various species of Pseudomonas. In prokaryotic systems, plasmids are used that contain replication sites and control sequences derived from a species compatible with a host cell. Transcription control sequences can include, but are not limited to promoters, operators, and enhancers. Expression systems useful in eukaryotic host cells comprise promoters derived from appropriate eukaryotic genes. Useful mammalian promoters include early and late promoters from SV40 or other viral promoters such as those derived from baculovirus, polyoma virus, adenovirus, bovine papilloma virus or avian sarcoma virus. Preferred transcription control sequences include those which function in bacterial, yeast, helminth or other parasite, insect and mammalian cells, such as, but not limited to, tac, lac, trp, trc, oxy-pro, omp/lpp, rrnB, bacteriophage lambda (λ), bacteriophage T7, T7lac, bacteriophage T3, bacteriophage SP6, bacteriophage SP01, metallothionein, α-mating factor, Pichia alcohol oxidase, alphavirus subgenomic promoters, antibiotic resistance gene, baculovirus, *Heliothis zea* insect virus, vaccinia virus, herpesvirus, poxvirus, adenovirus, cytomegalovirus, intermediate early promoters, simian virus 40, retrovirus, actin, retroviral long terminal repeat, Rous sarcoma virus, heat shock, phosphate and nitrate transcription control sequences, as well as other sequences capable of controlling gene expression in prokaryotic or eukaryotic cells.

The transcription step of the present method is performed in the presence of a guanosine nucleotides. Preferably, the transcript step is performed using guanosine monophosphates (GMP) and guanosine triphosphates (GTP). According to the present invention, the presence of guanosine mononucleotides enables the formation of linear RNA having a 5' end comprising a monophosphate (pN). The guanosine mononucleotides in the transcription step enables elongation of linear RNA molecules. Preferably, GMP and GTP are present at about a 1:1 ratio, more preferably about a 5:1 ratio, and even more preferably about a 10:1 ratio.

An oligonucleotide of the ligation step of the present method can comprise any DNA composition or structure that enables the oligonucleotide to anneal to the 5' and 3' ends of an RNA molecule transcribed from the DNA plasmid of step (1). The nucleic acid sequence of an oligonucleotide of the present invention can vary as extensively as the RNA sequence to which the oligonucleotide is to be annealed. One of skill in the art can ascertain an appropriate oligonucleotide sequence by determining the complementary sequence to the RNA, typically by using the sequence of the plasmid DNA used to produce the RNA. Preferably, a portion of the 3' end of an oligonucleotide is complementary to a portion of the 5' end of an RNA, and a portion of the 5' end of an oligonucleotide is complementary to a portion of the 3' end of an RNA. An oligonucleotide of the present invention can contain an additional "intermediary" sequence that is not complementary to an RNA, such intermediary sequence being located within (i.e., not at the end of) the oligonucleotide. An intermediary sequence of the present invention can comprise 10 base pair, preferably 5 base pairs, and even more preferably 2 base pairs.

The length of an oligonucleotide of the present invention can vary depending upon the RNA being ligated. Suitable oligonucleotides of the present invention are long enough to stably anneal with an RNA but short enough to separate from the RNA after the ligation step is complete, if such separation is desired. Preferably, an oligonucleotide of the present invention is from about 10 base pair to about 70 base pair, more preferably about 20 base pair to about 60 base pair, and even more preferably about 30 base pair to about 50 base pair in length.

In a preferred embodiment, an oligonucleotide of the present invention comprises a nucleic acid sequence including, 5' GGG CGG AAT TCC GGT CTC CCT GGG GAT CCT CTA GAG GAT A 3' (SEQ ID NO:1) and 5' ACC CCA GAG CTG TTT TAA CCT GGG GAT CCT CTA GAA TCG A 3' (SEQ ID NO:2).

Preferably, a circular RNA is formed in the ligation step of the present method by the addition of DNA ligase to annealed RNA/DNA oligonucleotide complexes. The method of the present invention can further comprise the step of separating DNA oligonucleotides from circular RNA following the ligation step. A separation step of the present method can be performed using any RNA/DNA separation (e.g., denaturing) methods known to those of skill in the art. For example, circular RNA can be separated from DNA oligonucleotides by denaturing gel electrophoresis. Under the denaturing gel conditions, oligonucleotides separate from circular RNA during electrophoresis, with the oligonucleotides migrating faster on the gel than the circular RNA. The circular RNA can then be recovered from the gel, separate from the oligonucleotides. One of skill in the art will recognize that separation of oligonucleotides from circular RNA can be less than complete. As such, it is within the scope of the invention that portions of the DNA from which circular RNA is derived can remain annealed to the RNA, thereby producing a hybrid RNA/DNA molecule.

A polypeptide of the present invention is produced by translating a circular RNA of the present invention to produce the polypeptide and recovering the polypeptide. In one embodiment, the translation step is performed in a cell. According to the present invention, a host cell is transformed with one or more circular RNAs to form a recombinant cell of the present invention. Transformation of a circular RNA into a cell can be accomplished by any method by which an RNA molecule can be inserted into a cell. Transformation techniques include, but are not limited to, transfection, electroporation, microinjection, lipofection, adsorption, and protoplast fusion. A recombinant cell may remain unicellular or may grow into a tissue, organ or a multicellular organism. Suitable and preferred circular RNA with which to transform a cell are as disclosed herein.

It is within the skill of one in the art to vary the number of circular RNA transformed into a cell to achieve and/or maximize production of a desired polypeptide. One of skill in the art can determine the amount of circular RNA to use based upon the type of cell being transformed, the method of transformation and the type and desired quantity of polypeptide to be produced. Preferably, a mammalian host cell is transformed with at least about $1 \times 10^5$ circular RNA molecules, more preferably at least about $5 \times 10^5$ circular RNA molecules, and even more preferably at least about $5 \times 10^6$ circular RNA molecules.

Suitable host cells to transform include any cell that can be transformed with a circular RNA of the present invention. Host cells can be either untransformed cells or cells that are already transformed with at least one circular RNA. Host cells of the present invention either can be endogenously (i.e., naturally) capable of producing a polypeptide of the present invention or can be capable of producing such polypeptides after being transformed with at least one circular RNA of the present invention. Host cells of the present invention can be any cell capable of producing at least one polypeptide of the present invention, and include bacterial, fungal (including yeast), parasite (including helminth, protozoa and ectoparasite), insect, other animal and plant cells. Preferred host cells include mammalian and yeast cells. More preferred host cells include COS cells, kidney cell lines, other fibroblast cell lines (e.g., human, murine or chicken embryo fibroblast cell lines), myeloma cell lines, Chinese hamster ovary cells, mouse NIH/3T3 cells, HeLa cells, and Jurkat cells. Particularly preferred host cells are COS cells and NIH/3T3 cells.

In accordance with the present invention, recombinant cells of the present invention can be used to produce one or more polypeptides of the present invention by culturing such cells under conditions effective to produce such a polypeptide, and recovering the polypeptide. Effective conditions to produce a polypeptide include, but are not limited to, appropriate media, bioreactor, temperature, pH and oxygen conditions that permit protein production. An appropriate, or effective, medium refers to any medium in which a cell of the present invention, when cultured, is capable of translating a circular RNA of the present invention. Such a medium is typically an aqueous medium comprising assimilable carbon, nitrogen and phosphate sources, as well as appropriate salts, minerals, metals and other nutrients, such as vitamins. When culturing a mammalian cell, the medium may comprise complex nutrients, vitamins and serum derived from a bovine or a fetal calf. A medium for culturing mammalian cells can also contain growth factors suitable for assisting the growth of such cells.

Cells of the present invention can be cultured under conventional conditions dependent upon the type of recombinant cell being cultured. For example, bacterial, algal, yeast and other fungal cells can be cultured in fermentation bioreactors, which include, but are not limited to, batch, fed-batch, cell recycle, and continuous fermentors. Mammalian cells can be cultured under standard tissue culture conditions in roller flasks, stationary tissue culture flasks, test tubes, microtiter dishes, and petri plates. Culturing is carried out at a temperature, pH and oxygen content appropriate for the recombinant cell. Such culturing conditions are well known and are within the expertise of one of ordinary skill in the art.

According to the present invention, polypeptides produced by a recombinant cell can be accumulated by culturing the recombinant cell in an effective culture or fermentation medium. In one embodiment, a recombinant cell is cultured to accumulate a polypeptide until a concentration the polypeptide exceeds the concentration of the polypeptide in a non-transformed cell. Preferably, the concentration of the polypeptide in the recombinant cell is about 10%, more preferably about 5% and even more preferably about 2% of the total protein of a cell.

In another embodiment, a recombinant cell is cultured for a suitable length of time to accumulate a polypeptide. A suitable length of time can include the time for which a cell remains alive and actively producing the polypeptide. Preferably, mammalian cells transformed with a circular RNA of the present invention are cultured for from about 1 hour to 72 hours, more preferably from about 3 hours to 64 hours, and even more preferably from about 6 hours to 48 hours.

Depending on the polypeptide produced, the polypeptide may either remain within the recombinant cell or be secreted into the culture medium. The phrase "recovering the polypeptide" refers simply to collecting the whole culture medium containing the polypeptide and need not imply additional steps of separation or purification. Polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Polypeptides of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and should be capable of stimulating the production of antibodies in a treated animal.

It is within the scope of the present invention that a circular RNA can include a RNA sequence that encodes a "tag" useful for the isolation of a polypeptide encoded by the RNA. Suitable tags for use with the present invention include any molecule that can bind to a reagent bound to a solid substrate. Examples of tags include, fusion segments, such as glutathione binding domains (e.g., glutathione-S-transferase) capable of binding to glutathione; a metal binding domain, (e.g., a poly-histidine segment capable of binding to a divalent metal ion); an immunoglobulin binding domain (e.g., Protein A, Protein G, T cell, B cell, Fc receptor or complement protein antibody-binding domains); a sugar binding domain (e.g., a maltose binding domain from a maltose binding protein); peptides; at least a portion of β-galactosidase, a strep tag peptide; and/or other domains that can be purified using compounds that bind to a domain (e.g., monoclonal antibodies). Preferred tags include a strep tag peptide, a β-galactosidase tag and a peptide.

In another embodiment, the translation step is performed in a cell-free system. According to the present invention, one or more circular RNAs are translated in a polypeptide synthesizing system containing reagents necessary for RNA translation. Suitable reagents for a cell-free system of the present invention include, but are not limited to, ribosomes, tRNAs and protein synthesis factors. Suitable cell-free systems of the present invention include cell extracts from which substantially all of the cellular RNA has been removed. Preferably, such cell-free systems are derived from reticulocyte cells, wheat germ cells and Human Hela cells. Translation of circular RNA in a cell-free system can be achieved using methods standard in the art. Preferably, at least about 2 microgram (µg) of circular RNA is added to at least about 35 microliter (µl) reticulocyte lysate, more preferably at least about 1 µg of circular RNA is added to at least about 15 µl reticulocyte lysate, and even more preferably at least about 0.5 µg of circular RNA is added to at least about 8.5 µl reticulocyte lysate.

According to the present invention, polypeptides produced in a cell-free system can be accumulated by incubating the circular RNA in a polypeptide synthesizing system for a suitable length of time, preferably for as long as the protein synthesis factors can support polypeptide translation. Preferably, a circular RNA is incubated in a cell-free system for from about 10 minutes to about 240 minutes, more preferably for from about 20 minutes to about 180 minutes, and even more preferably for from about 30 minutes to about 120 minutes. Polypeptides produced in a cell-free system of the present invention can be recovered using any of various recovery methods known in the art, in particular any recovery method described herein.

A polypeptide of the present invention can then be produced by culturing a yeast cell containing a circular RNA under effective culture conditions.

In another embodiment, the present invention includes a method to continuously translate a RNA molecule, comprising: (1) providing a circular RNA molecule having an internal ribosome entry site element, and lacking a UAA, UGA or UAG codon; and (2) translating said RNA molecule for a sufficient amount of time to allow more than one round of translation. As used herein, a "continuous translation" refers to translating more than one polypeptide from a single RNA circle. Continuous translation can be detected by the presence of increasingly larger polypeptide chains, in which the largest polypeptide chain is greater than the predicted size for a single polypeptide within the chain. Also, as used herein, a "round of translation" refers to the migration of a ribosome completely around a RNA circle. The number of rounds of translation can be determined by the concentration of polypeptide chain produced during the translation step of the present method. Preferably, the translation step of the present method is carried out for at least about 15 minutes, more preferably at least about 30 minutes, and even more preferably at least about 45 minutes, if the translation step is performed in a cell-free system using rabbit reticulocyte lysates at 30° C.

In another aspect of the present invention, a circular RNA can be used to produce a delivery vehicle capable of delivering the circular RNA to a cell or an organism. A delivery vehicle of the present invention comprises one or more circular RNA of the present invention combined with a pharmaceutically acceptable carrier. As used herein, a "carrier" refers to any substance suitable as a vehicle for delivering a circular RNA of the present invention to a suitable in vivo or in vitro site. As such, carriers can act as a pharmaceutically acceptable excipient of a therapeutic composition containing a circular RNA of the present invention. Preferred carriers are capable of maintaining a circular RNA of the present invention in a form that, upon arrival of the circular RNA to a cell, the circular RNA is capable of entering the cell and being translated by the cell. Carriers of the present invention include: (1) excipients or formularies that transport, but do not specifically, target a circular RNA to a cell (referred to herein as non-targeting carriers); and (2) excipients or formularies that deliver a circular RNA to a specific site in an animal or a specific cell (i.e., targeting carriers). Examples of non-targeting carriers include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- and o-cresol, formalin and benzol alcohol. Preferred auxiliary substances for aerosol delivery include surfactant substances non-toxic to an animal, for example, esters or partial esters of fatty acids containing from about six to about twenty-two carbon atoms. Examples of esters include, caproic, octanoic, lauric, palmitic, stearic, linoleic, linolenic, olesteric, and oleic acids. Other carriers can include metal particles (e.g., gold particles) for use with, for example, a biolistic gun through the skin.

Targeting carriers of the present invention are capable of delivering a circular RNA of the present invention to a target site in an animal. A "target site" refers to a site in an animal to which one desires to deliver a circular RNA. For example, a target site can be a cell, or an area around a cell, involved in a disease. Examples of targeting carriers include, but are not limited to, artificial and natural lipid-containing delivery vehicles. Natural lipid-containing target carriers include cells and cellular membranes. Artificial lipid-containing target carriers include liposomes and micelles. A target carrier of the present invention can be modified to target to a particular site in an animal, thereby targeting and making use of a circular RNA of the present invention at that site. Suitable modifications include manipulating the chemical formula of the lipid portion of the target carrier and/or introducing into the carrier a compound capable of specifically targeting a carrier to a preferred site, for example, a preferred cell type. Specifically, targeting refers to causing a target carrier to bind to a particular cell by the interaction of the compound in the carrier to a molecule on the surface of the cell. Suitable targeting compounds include ligands capable of selectively (i.e., specifically) binding another molecule at a particular site. Examples of such ligands include antibodies, antigens, receptors and receptor ligands. For example, an antibody specific for an antigen found on the surface of a cell can be introduced to the outer surface of a liposome so as to target the liposome to the cell. Useful ligands can be selected by one skilled in the art based upon the purpose of the delivery of the carrier (e.g., based on the disease being treated using the target carrier). Manipulating the chemical formula of the lipid portion of a target carrier can modulate the extracellular or intracellular targeting of the carrier. For example, a chemical can be added to the lipid formula of a liposome that alters the charge of the lipid bilayer of the liposome so that the liposome fuses with particular cells having particular charge characteristics.

A preferred target carrier of the present invention is a liposome. A liposome is capable of remaining stable in an animal for a sufficient amount of time to deliver a circular RNA of the present invention to a preferred site in the animal. A liposome of the present invention is preferably stable in the animal into which it has been administered for at least about 30 minutes, more preferably for at least about 1 hour and even more preferably for at least about 24 hours. A liposome of the present invention comprises a lipid composition that is capable of targeting a nucleic acid molecule of the present invention to a particular, or selected, site in an animal.

Complexing a liposome with a circular RNA of the present invention can be achieved using methods standard in the art (see, for example, using Lipofectin, obtained from GIBCO BRL, Gaithersburg, Md.). A suitable concentration of a circular RNA of the present invention to add to a liposome includes a concentration effective for delivering a sufficient amount of circular RNA to a cell such that the cell can produce sufficient polypeptide to effect a disease state.

In another aspect of the present invention, is a method to treat an animal using a circular RNA, comprising administering to an animal an effective amount of a circular RNA comprising an internal ribosome entry site element of the present invention, operatively linked to an RNA sequence encoding a polypeptide, wherein the circular RNA is translated to produce the polypeptide in the animal to treat the animal. The present method is useful for the treatment of any disease that can be treated by the administration of a polypeptide to an animal. Such diseases include pathogen-induced diseases (e.g., those caused by viruses, animal parasites and bacteria), metabolic diseases, immunological diseases, hormonal disease, neurological diseases, respiratory diseases, circulatory diseases and other related disease states that involve particular biological functions.

Acceptable protocols to administer a circular RNA in an effective manner include individual dose size, number of doses, frequency of dose administration, and mode of administration. Determination of such protocols can be accomplished by those skilled in the art depending upon a variety of variables, including the animal to be treated, whether the circular RNA is being administered as a vaccine, a toleragen and/or as a treatment for an existing disease. The manner of administration of a circular RNA of the present invention can depend upon the particular purpose for the delivery, the carrier associated with the RNA, the overall health and condition of the recipient and the judgement of the physician or technician administering the circular RNA or the delivery vehicle. A circular RNA of the present invention can be administered to an animal using a variety of methods. Such delivery methods can include parenteral, topical, oral or local administration, such as intradermally or by aerosol. A circular RNA can be administered in a variety of unit dosage forms depending upon the method of administration. For example, unit dosage forms suitable for oral administration to the intestinal region of an animal include powder, tablets, pills and capsules. A circular RNA of the present invention can be administered to any animal, preferably to mammals, and more preferably to humans.

The following examples are provided for the purposes of illustration and are not intended to limit the scope of the present invention.

EXAMPLES

Example 1

This example describes the production of DNA plasmids to be used to prepare circular RNA.

An NcoI-NheI DNA fragment containing base pairs 1957 to 2471 of the polioviral genome was ligated into plasmid p5'NC-LUC (described in detail in Hambridge et al., *J. Virol.* 65:6312, 1991), which had been digested with NcoI and NheI. All restriction enzyme digestion and ligation steps performed herein were done using methods known to those of skill in the art. The plasmid p5'NC-LUC was then digested with NcoI and XbaI to yield plasmid p5'NC-VP3. A T7 RNA polymerase promoter and an encephalomyocarditis virus internal ribosome entry site (EMCV-IRES; R strain) was then inserted into the p5'NC-VP3A plasmid by isolating a PvuII-NcoI DNA fragment that contained a T7

RNA polymerase promoter and an EMCV-IRES from pCITE-1 (obtained from Novagen, Madison, Wis.). The isolated PvuII-NcoI DNA fragment was then ligated to plasmid p5'NC-VP3, which had been digested with PvuII and NcoI to yield plasmid pEMCV-IRES/VP3. A plasmid lacking an IRES element was constructed by replacing the EMCV-IRES in pEMCV-IRES/VP3 with base pairs 1 to 70 of a poliovirus complementary DNA (cDNA) to yield pΔ5'NC/VP3.

To determine whether continuous translation could be obtained from a circular RNA, a DNA plasmid was constructed in which several stop codons present in the wild-type EMCV-IRES were eliminated by inserting an EMCV-IRES element with an open reading frame (EMCV-ORF-IRES/VP3). A PvuII-NcoI fragment from pCITE-1 was ligated into the plasmid p5'NC-LUC, which had been digested with PvuII and NcoI to yield the plasmid pEMCV-IRES/LUC. The plasmid pEMCV-IRES/LUC was then partially digested with EcoRI and then digested into completion with SmaI. The EcoRI-SmaI fragment containing the DNA encoding EMCV-IRES and LUC was isolated, and overhanging sequence at the ends of the fragment were removed using Klenow enzyme according to methods standard in the art. In parallel, the plasmid pCV (described in detail in Tsukiyama-Kohara, *J. Virol.* 66:1476, 1992) containing a chloramphenicol acetyltransferase (CAT) gene was digested with XbaI and SalI. The XbaI-SalI fragment containing the CAT gene was isolated, and the overhanging sequence at the ends of the fragment were removed using Klenow. The EcoRI-SmaI fragment containing the DNA encoding EMCV-IRES and LUC and the XbaI-SalI fragment containing the CAT gene were ligated to yield the plasmid pCAT/EMCV-IRES/LUC, which contains a promoter for T7 RNA polymerase upstream of the CAT gene. To construct a plasmid lacking an IRES element, the plasmid pCAT/EMCV-IRES/LUC was digested with AVRII and HindIII to remove a 69 base pair fragment containing base pairs 415 to 484 in the IRES element. The remaining larger fragment were treated with Klenow and the ends of the fragment religated to form the plasmid pCAT/ΔEMCV-IRES/LUC.

A dicistronic plasmid containing a CAT coding region followed by the EMCV-open reading frame IRES and a luciferase coding region, referred to herein as plasmid pCAT/EMCV-ORF-IRES/LUC, was produced by the method described in Macejak et al. (ibid.). The plasmid pCAT/EMCV-ORF-IRES/LUC is identical to pCAT/EMCV-IRES/LUC except for the introduction of the following base pair changes in the EMCV-IRES and the presence of sequences encoding a thrombin cleavage site (described in detail in Chang, *Eur. J. Biochem.* 151:217, 1985); base pair 493 (G was changed to C), base pair 585 (A to C), base pair 759 (T to C), and base pair 780 (T to C). These changes were introduced with the use of the Transformer site-directed mutagenesis method (Clontech Laboratories, Palo Alto, Calif.). The thrombin cleavage site (Chang, ibid.) was inserted by replacing the polycytidine sequences present at the 5' end of the EMCV-IRES (described in detail in Duke et al., *J. Virol.* 66:1602, 1992). This step was performed by polymerase chain reaction (PCR) amplification of DNA encoding the EMCV-IRES using a first primer specific for base pairs 309 to 337 of the EMCV-IRES and a second primer specific for base pairs 409 to 427 of the EMCV-IRES. The presence of all expected mutations was confirmed by DNA sequencing using standard sequencing methods.

Example 2

This example describes the production of circular RNA.

Plasmid DNAs described above in Example 1 were linearized with SmaI using standard digestion methods. The linearized double stranded DNA plasmids were transcribed using the method generally described in Sambrook et al. (ibid.) at pages 10.32 and 10.33. In order to produce RNA fragments have monophosphate groups at the 5' end, the method of Sambrook et al. was modified to include guanosine monophosphate (GMP) and guanosine triphosphate (GTP) at a 10:1 ratio.

The free 5' and 3' ends of the RNA transcripts were annealed as follows. RNA transcripts were annealed to appropriate DNA oligonucleotides by heating a mixture of RNA and oligonucleotides to 92° C. for 1 minute and then allowed to cool to room temperature. Transcripts produced using pEMCV-IRES/VP3 were annealed using an oligonucleotide having the nucleic acid sequence 5' ACC CCA GAG CTG TTT TAA CCT GGG GAT CCT CTA GAA TCG A 3' (SEQ ID NO:1). Transcripts produced using pΔ5'NC/VP3 were annealed using an oligonucleotide having the nucleic acid sequence 5' ACC CCA GAG CTG TTT TAA CCT GTG GAT CCT CTA GAA TCG A 3' (SEQ ID NO:2).

Figure 1:
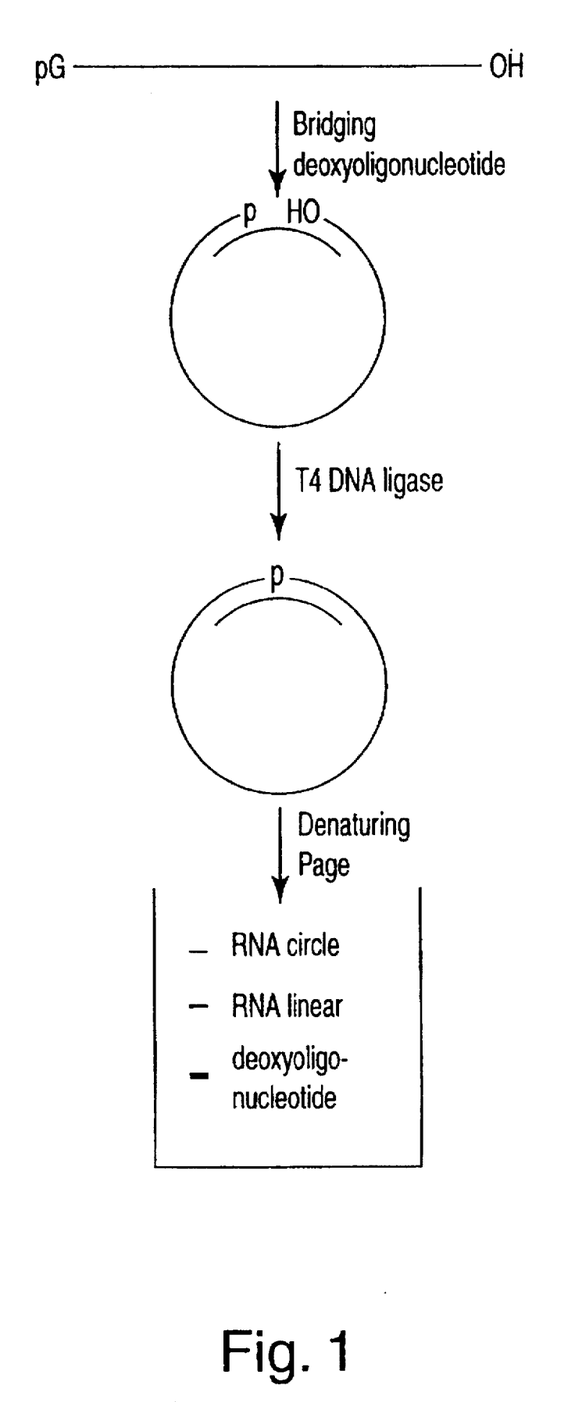
FIG. 1 provides a schematic outline of the synthesis of circular RNAs with the use of linear RNAs synthesized in vitro using bridging deoxyoligonucleotides complementary to both the 5' and 3' ends of and RNA, and T4 DNA ligase.

After the oligonucleotides were annealed to their respective RNA transcripts, the 5' and 3' ends of the RNA transcripts were ligated using the following method. About 2 μM RNA/oligonucleotide complex was incubated in ligase buffer [50 mM Tris-HCl (pH 7.5), 10 mM MgCl$_2$, 20 mM dithiothreitol, 1 mM ATP, 50 μg/ml bovine serum albumin, 1 units/μl T4 DNA ligase (United States Biochemical)] for 4 hours at 25° C. The ligation step is schematically represented in FIG. 1.

The successful production of circular RNA was tested by resolving the ligated RNA and oligonucleotide mixtures on a 4.5% denaturing polyacrylamide gel, containing 8M urea, by electrophoresis (the method being generally described in Moore et al., *Science* 256: 992–997, 1992). The bottom of FIG. 1 shows a representation of the resulting gel.

To confirm the production of circular RNA, linear RNA transcripts to be circularized were labeled at their 5' ends with $^{32}$P using T4 polynucleotide kinase according to methods standard in the art. Ligated RNA samples were purified by denaturing polyacrylamide gel electrophoresis. About $10^3$ cpm of RNA was then treated with 1 unit of calf intestine phosphatase (CIP; 1 U/μl) at 37° C. for 30 minutes. The CIP treated samples were analyzed on a 4.5% denaturing polyacrylamide gel. The results indicated that linear 5'-radiolabeled RNA could be dephosphorylated after incubation with CIP. In contrast, ligation of linear 5'-radiolabeled RNA resulted in a more slowly migrating RNA species that was resistant to phosphatase treatment. Thus, the results indicate that the low-mobility RNA species represents circular RNA.

Example 3

This example describes the synthesis of defined protein products from circular RNA substrates, with or without an IRES element, using eukaryotic ribosomes.

To test whether RNA circles could direct the synthesis of a defined protein, translation products were synthesized after incubation of linear and circular RNAs products of pEMCV-IRES/VP3 and pΔ5'NC/VP3 in a rabbit reticulocyte lysate. About 0.5 μg of polyacrylamide gel-purified linear or circular RNAs, made according to the method of Example 2, were combined with about 8.5 μl rabbit reticulocyte lysate (Flexi-system, Promega, Madison, Wis.) and about 0.75 µl of ($^{35}$S)methionine (100 Ci/mmol; Amersham, Arlington Heights, Ill.) in a 12.5 µl reaction volume. The reaction mixture was incubated for about 45 minutes at 30° C. In the reaction mixtures having RNA products of pEMCV-IRES/VP3, the concentration of KCl was about 120 mM. About 4 µl aliquots of each reaction mixture was analyzed on 15% SDS-polyacrylamide gels.

Figure 2:
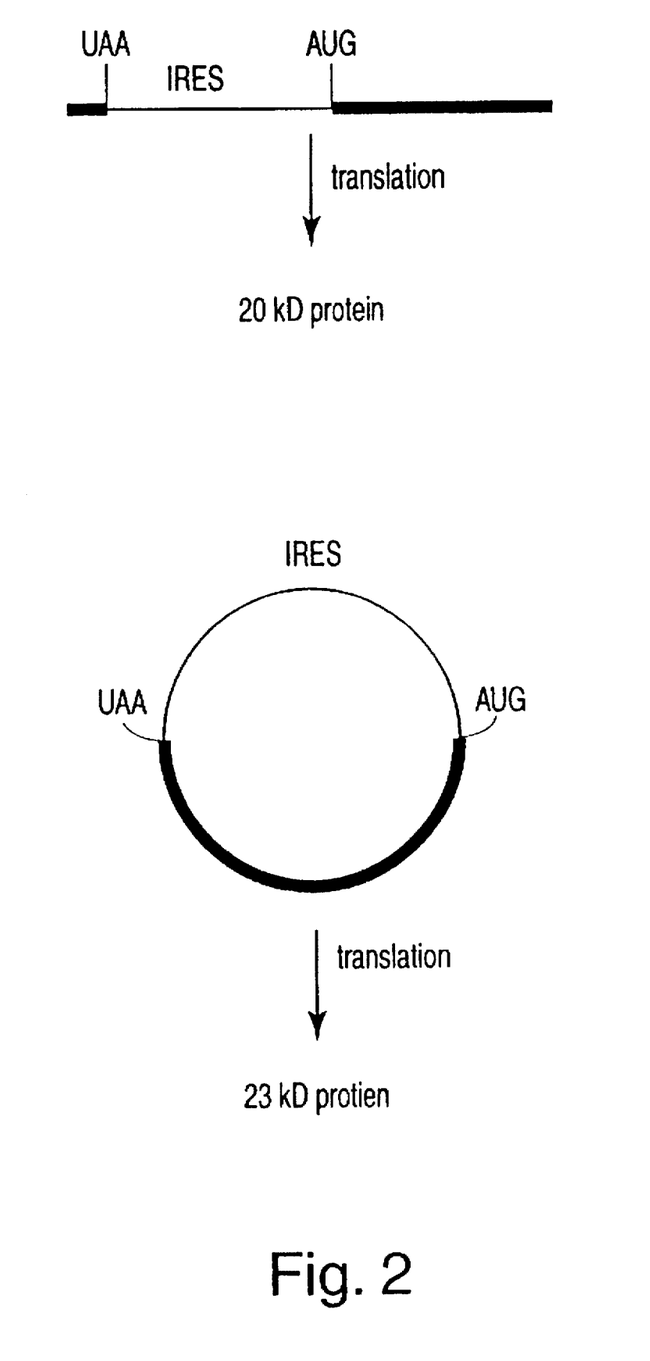
FIG. 2 illustrates the predicted sizes of protein products translated in vitro from linear or circular RNAs containing the IRES element of EMCV.

The predicted size of protein products translated in vitro from linear or circular RNA products of pEMCV-IRES/VP3 containing the IRES element of EMCV are illustrated in FIG. 2 and were calculated as follows. A segment of the capsid VP3 gene of poliovirus (base pairs 1957 to 2471) and an additional 13 base pairs of polylinker sequence constituted the coding region for an approximately 20 kD protein. After circularization, the coding region was predicted to extend into the EMCV 5' noncoding region, resulting in an open reading frame (ORF) encoding a 23 kD protein. Initiator AUG codons, terminator UAA codons, and the location of the IRES are also indicated in FIG. 2. The VP3 coding region is indicated by the thick line.

Translation of linear RNA products of pEMCV-IRES/VP3 produced a 20 kD product. After circularization, however, RNA products of pEMCV-IRES/VP3 directed the synthesis of the predicted 23 kD protein product. In contrast, linear and circular RNA products of pΔ5'NC/VP3, lacking an IRES element, did not direct the synthesis of a detectable protein product. Even a randomly cleaved linear RNAs that are always present in preparations of circular RNAs, that lacked an IRES element, did not direct the synthesis of a discrete protein products. Thus, circular RNA can direct synthesis of a protein product having the predicted size.

Example 4

This example describes the translation of dicistronic RNA products indicating internal initiation.

To test for internal initiation of protein products of dicistronic RNAs containing EMCV-IRES/VP3, EMCV-ORF-IRES and no IRES in the intercistronic space region, respectively, were examined using the method of Example 3. The translation products were analyzed by SDS-PAGE as in Example 3. Analysis of translation products of RNA products of pCAT/EMCV-ORF-IRES/LUC indicated the presence of a protein product of about 27 kD (CAT protein), thereby indicating that RNA products of pCAT/EMCV-ORF-IRES/LUC directed the synthesis of CAT protein, the product of the first cistron. In addition, analysis of protein products of dicistronic RNA containing EMCV-IRES and EMCV-ORF-IRES between CAT and LUC cistrons indicated that the second LUC cistron was translated from these RNAs. In contrast, the RNA containing a 70 base pair deletion near the 5' end of the IRES element (Δ5'NC) did not direct the synthesis of the second cistron (luciferase). Thus, the EMCV-ORF IRES element can direct internal initiation in linear RNA molecules.

Example 5

This example describes the translation of circular RNA molecules encoding thrombin cleavage sites.

Figure 3:
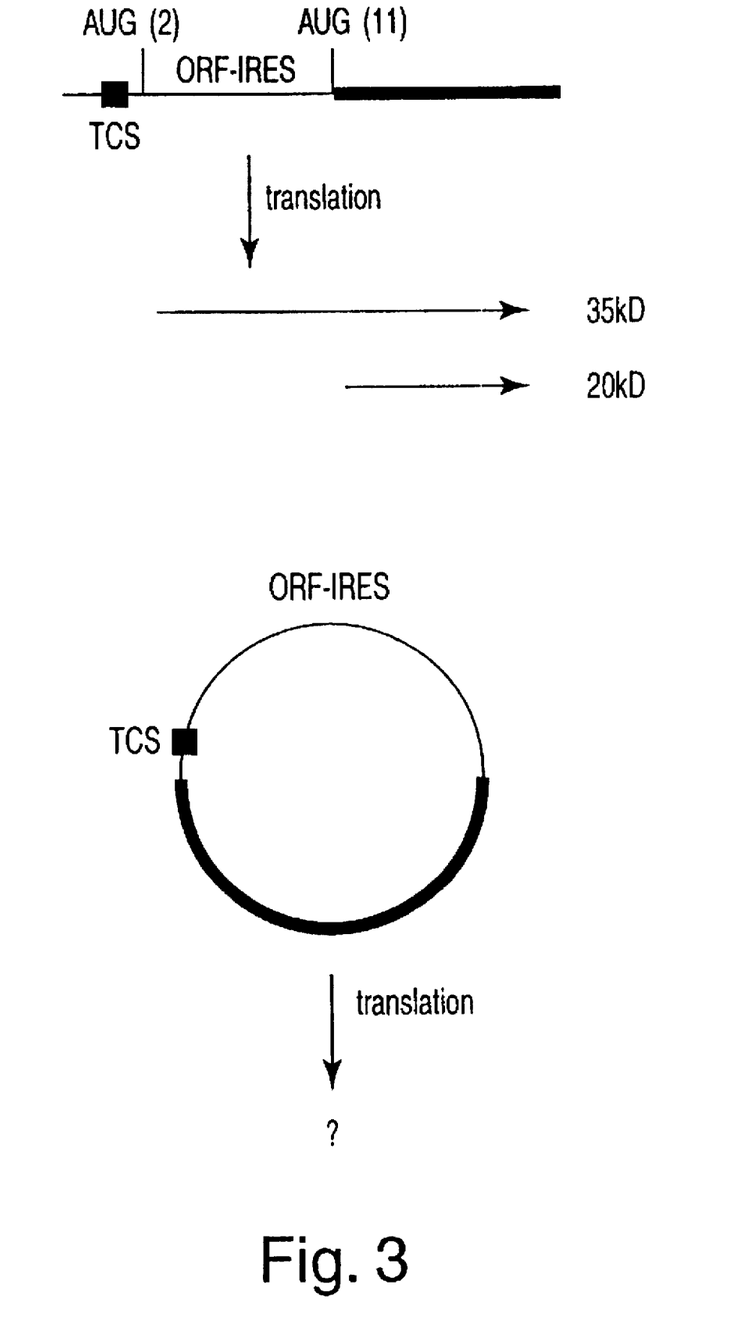
FIG. 3 illustrates the predicted sizes of protein products translated in vitro from linear or circular RNAs containing the EMCV-ORF IRES element.

To test the function of the EMCV-ORF IRES element in a circular RNA molecule, the translation products of linear and circular EMCV-ORF IRES RNAs, either treated or not treated with thrombin were analyzed. Referring to FIG. 3, the positions of two initiator AUGs are schematically illustrated; AUG(2) is predicted to be the translational start codon for ribosomes entering the RNA at the 5' end, and AUG(11) is predicted to be the start codon for ribosomes entering the RNA by the IRES. The predicted translation products are about 35 kD and 20 kD, and the location of the thrombin cleavage site (TCS) is indicated. The VP3 coding region is indicated by the thick line.

Linear and circular RNA products of pCAT/EMCV-ORF-IRES/LUC were translated in a rabbit reticulocyte lysate as described in Example 3. After completion of the translation reactions, about 100 µg/ml of ribonuclease A and about 100 units/ml of ribonuclease T1 were added to digest the RNA templates. About 1/10 of the reaction mixture was then incubated with 1 NIH unit of thrombin (obtained from Sigma, St. Louis, Mo.) in 20 µl of thrombin buffer [50 mM Tris-HCl (pH 8.0), 150 mM NaCl, 2.5 mM CaCl and 0.1% β-mercaptoethanol] for about 8 hours at 25° C. The products of the thrombin digestion were analyzed on a 15% SDS-polyacrylamide gel. The polyacrylamide gel analysis indicated that linear EMCV-ORF IRES RNAs directed the synthesis of two protein products, 35 kD and 20 kD in size. The 35 kD product was synthesized by 5' end-dependent scanning, in which the AUG(2) codon in the EMCV-ORF IRES (the first AUG codon in a favorable context for translational initiation) was used as the start codon. The 20 kD product was synthesized by ribosomes recruited onto the RNA by the EMCV-ORF IRES, in which the AUG(2) codon in the EMCV-ORF IRES was used as the start codon.

Figure 4:
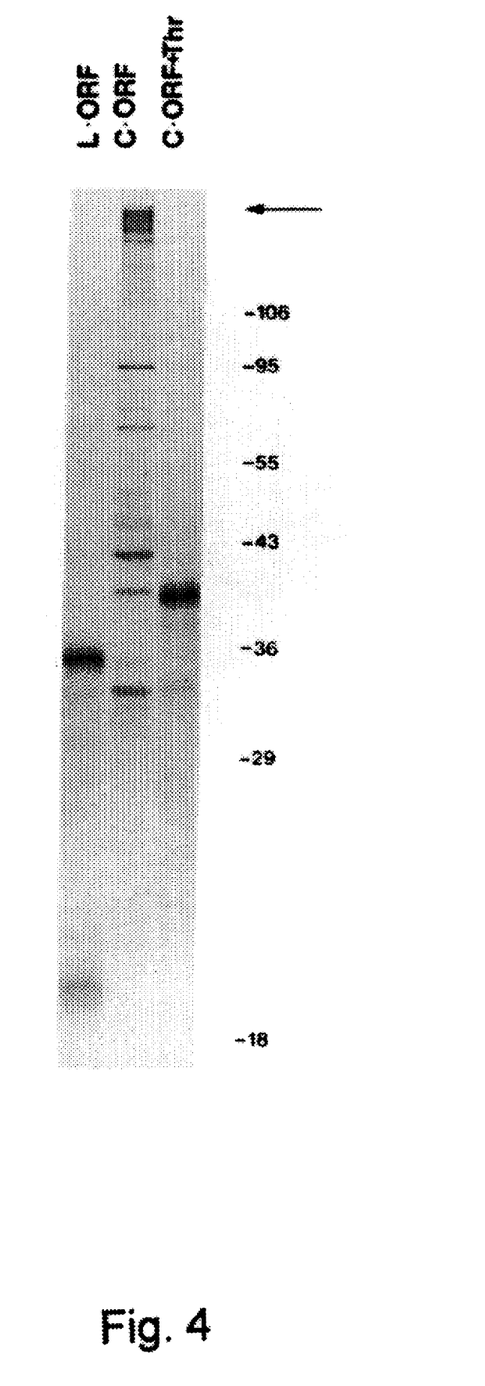
FIG. 4 illustrates the protein product resulting from continuous translation of IRES-containing RNA molecules.

Referring to FIG. 4, circular EMCV-ORF IRES RNAs directed the synthesis of extremely long protein species, many of which were larger than 106 kD in size. Most of these products were larger than 40 kD, the largest protein that could be synthesized from monomeric linear RNA templates using the methods described in these Examples. These proteins resulted from synthesis by ribosomes traversing the circular RNA templates for multiple rounds. The possibility that the high molecular weight protein products were fortuitous aggregates of smaller proteins that resisted denaturation, rather than covalently linked multimers of 40 kD polypeptide, was excluded by demonstrating that, upon thrombin cleavage, the high molecular weight products were cleaved into 40 kD polypeptides. Thus, the eukaryotic translational apparatus can initiate and elongate continuous protein synthesis of IRES-containing circular RNAs in the absence of a free 5' end.

Taken together, the results of the preceding Examples indicate that IRES elements can recruit ribosomes onto IRES-containing RNAs without assistance from the capped or uncapped 5' ends in the RNA or from their associated cap-binding protein factors. In addition, the spatial constraints imposed by circularization of IRES-containing RNA molecules did not interfere with IRES function. Thus, circular RNA of the present invention can serve as substrates for eukaryotic ribosomes and can initiate continuous translation of protein products from such circular RNAs.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

GGGCGGAATT CCGGTCTCCC TGGGGATCCT CTAGAGGATA     40

( 2 ) INFORMATION FOR SEQ ID NO:2:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

ACCCCAGAGC TGTTTTAACC TGTGGATCCT CTAGAATCGA     40

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. A circular RNA comprising an internal ribosome entry site (IRES) element that engages an eukaryotic ribosome.

2. The circular RNA of claim 1, wherein said circular RNA is at least about 100 base pairs in length.

3. The circular RNA of claim 1, wherein said circular RNA is at least about 500 base pairs in length.

4. The circular RNA of claim 1, wherein said circular RNA is at least about 1,000 base pairs in length.

5. The circular RNA of claim 1, wherein said circular RNA is more stable than linear RNA when incubated with exonuclease.

6. The circular RNA of claim 1, wherein the conformation of said circular RNA does not sterically hinder the translation of said circular RNA.

7. The circular RNA of claim 1, wherein said circular RNA migrates more slowly than a linear RNA when resolved by electrophoresis using a 4.5% urea-containing polyacrylamide gel.

8. The circular RNA of claim 1, wherein said circular RNA is essentially not susceptible to dephosphorylation when said circular RNA is incubated with calf intestine phosphatase.

9. The circular RNA of claim 8, wherein said internal ribosome entry site element is at least about 250 base pairs in length.

10. The circular RNA of claim 9, wherein said internal ribosome entry site element is at least about 500 base pairs in length.

11. The circular RNA of claim 9, wherein said internal ribosome entry site element is selected from the group consisting of an IRES element derived from picornavirus cDNA, BiP-encoding DNA, Drosophila Antennapedia DNA, and bFGF-encoding DNA.

12. The circular RNA of claim 11, wherein said picornavirus DNA is selected from the group consisting of encephalomyocarditis virus cDNA, poliovirus cDNA and rhinovirus cDNA.

13. The circular RNA of claim 1, comprising an RNA sequence encoding a polypeptide.

14. The circular RNA of claim 13, wherein said polypeptide has repeating units.

15. The circular RNA of claim 13, wherein said polypeptide comprises more than one type of protein.

16. The circular RNA of claim 13, wherein said polypeptide comprises one or more proteolytic cleavage sites.

17. The circular RNA of claim 13, wherein said polypeptide is selected from the group consisting of at least a portion of a viral envelope protein, metabolic regulatory enzymes, a hormone, an antigen, a toleragen, a cytokine, a toxin, enzymes whose absence is associated with a disease, polypeptides that are not active in an animal until cleaved, β-keratin, collagen, elastin and mixtures thereof.

18. The circular RNA of claim 1, comprising an initiator AUG codon.

19. The circular RNA of claim 1, wherein said circular RNA comprises a RNA sequence selected from the group consisting of EMCV-IRES/VP3 and EMCV-ORF-IRES/VP3.

20. The circular RNA of claim 1, wherein said circular RNA is non-naturally-occurring.

21. The circular RNA of claim 1, wherein said circular RNA is derived in vitro from a DNA plasmid.

22. A recombinant cell comprising a circular RNA comprising an internal ribosome entry site element that engages an eukaryotic ribosome.

23. The recombinant cell of claim 22, wherein said RNA comprises an RNA sequence encoding a polypeptide.

24. The recombinant cell of claim 22, wherein said recombinant cell is derived from a host cell selected from the group consisting of bacterial, fungal, parasite, insect, animal and plant cells.

25. The recombinant cell of claim 22, wherein said recombinant cell is derived from a host cell selected from the group consisting of a Cos cell, kidney cell lines, other fibroblast cell lines, myeloma cell lines, Chinese hamster ovary cells, mouse NIH/3T3 cells, HeLa cells and Jurkat cells.

26. A delivery vehicle comprising a pharmaceutically acceptable carrier carrying a circular RNA comprising an internal ribosome entry site element that engages an eukaryotic ribosome.

27. The delivery vehicle of claim 26, wherein said delivery vehicle is selected from the group consisting of a physiologically balanced aqueous solution, a cell and a lipid construction.

28. The delivery vehicle of claim 27, wherein said cell is selected from the group consisting of Cos cell, kidney cell lines, other fibroblast cell lines, myeloma cell lines, Chinese hamster ovary cells, mouse NIH/3T3 cells, HeLa cells and Jurkat cells.

29. The delivery vehicle of claim 27, wherein said lipid construction is selected from the group consisting of a liposome, a micelle, and a cellular membrane.

30. The delivery vehicle of claim 27, wherein said delivery vehicle comprises a liposome.

31. A method for producing a polypeptide, comprising:

(a) translating a circular RNA comprising an internal ribosome entry site element operatively linked to an RNA sequence encoding a polypeptide to produce said polypeptide; and (b) recovering said polypeptide.

32. The method of claim 31, wherein said translation step is performed in a cell.

33. The method of claim 31, wherein said translation step is performed by transforming a cell with at least about $1 \times 10^5$ of said circular RNA and culturing said cell in an effective culture medium.

34. The method of claim 32, wherein said cell is a eukaryotic cell.

35. The method of claim 32, wherein said cell is selected from the group consisting of a Cos cell, kidney cell lines, other fibroblast cell lines, myeloma cell lines, Chinese hamster ovary cells, mouse NIH/3T3 cells, HeLa cells and Jurkat cells.

36. The method of claim 32, wherein said method further comprises accumulating said polypeptide by culturing said cell in an effective culture medium for from about 6 hours to about 48 hours.

37. The method of claim 31, wherein said translation step is performed in a cell-free system.

38. The method of claim 37, wherein said cell-free system comprises a reticulocyte lysate.

39. The method of claim 31, wherein said method further comprises accumulating said polypeptide by incubating said circular RNA in a reticulocyte lysate for from about 30 minutes to about 120 minutes when said incubation is performed at 30° C.

40. The method of claim 31, wherein said recovery step comprises isolating said polypeptide by a method selected from the group consisting affinity chromatography, ion exchange chromatography, electrophoresis, hydrophobic interaction chromatography, gel filtration chromatography, chromatofocusing, centrifugation, high pressure liquid chromatography, and dialysis.

41. A method to use a circular RNA for producing a polypeptide, comprising:

(a) transforming a cell with a circular RNA comprising an internal ribosome entry site element operatively linked to an RNA sequence encoding a polypeptide;

(b) translating said circular RNA to produce said polypeptide;

(c) accumulating said polypeptide until a concentration of said polypeptide exceeds the concentration of said polypeptide in non-transformed cells; and (d) recovering said polypeptide from said cells transformed with circular RNA.

42. A circular RNA capable of engaging an eukaryotic ribosome, said RNA produced by the method comprising:

(a) providing a linear DNA plasmid comprising a nucleic acid sequence that is transcribed into an internal ribosome entry site element;

(b) transcribing said DNA plasmid in the presence of guanosine nucleotide to produce linear RNA transcripts; and (c) ligating said transcripts with DNA oligonucleotides complementary to the 5' and 3' ends of said transcript to produce circular RNA.

43. The RNA of claim 42, wherein said further comprises separating said DNA oligonucleotides from said circular RNA.

44. The RNA of claim 42, wherein said DNA plasmid comprises poliovirus cDNA.

45. The RNA of claim 42, wherein said internal ribosome entry site element is derived from encephalomyocarditis virus cDNA.

46. The RNA of claim 42, wherein said oligonucleotide is from about 30 bp to about 50 bp in length.

47. The RNA of claim 42, wherein said oligonucleotide is selected from the group consisting of SEQ ID NO:1 and SEQ ID NO:2.

48. The RNA of claim 42, wherein said guanosine nucleotide is guanosine mononucleotide and guanosine trinucleotide.

49. The RNA of claim 48, wherein said guanosine mononucleotide and guanosine trinucleotide are present at about a 10:1 ratio.

* * * * *